US008084198B2

(12) United States Patent
Kozian et al.

(10) Patent No.: US 8,084,198 B2
(45) Date of Patent: Dec. 27, 2011

(54) USE OF A GIP PROMOTER POLYMORPHISM

(75) Inventors: Detlef Kozian, Frankfurt am Main (DE); Matthias Herrmann, Frankfurt am Main (DE); Karl-Ernst Siegler, Ludwigshafen (DE); Jean-Francois Deleuze, Paris (FR); Sylvain Ricard, Paris (FR); Sandrine Mace, Paris (FR)

(73) Assignee: Sanofi-Aventis, Paris (FR)

( * ) Notice: Subject to any disclaimer, the term of this patent is extended or adjusted under 35 U.S.C. 154(b) by 615 days.

(21) Appl. No.: 11/913,873

(22) PCT Filed: May 3, 2006

(86) PCT No.: PCT/EP2006/004141
§ 371 (c)(1),
(2), (4) Date: May 2, 2008

(87) PCT Pub. No.: WO2006/119905
PCT Pub. Date: Nov. 16, 2006

(65) Prior Publication Data
US 2008/0312098 A1    Dec. 18, 2008

(30) Foreign Application Priority Data
May 11, 2005 (EP) .................................... 05010223

(51) Int. Cl.
*C12Q 1/68* (2006.01)
*C12P 19/34* (2006.01)
*C07H 21/04* (2006.01)
(52) U.S. Cl. .......... 435/6; 435/91.2; 536/24.3; 536/23.1
(58) Field of Classification Search .................. None
See application file for complete search history.

(56) References Cited

U.S. PATENT DOCUMENTS

| 4,816,397 | A | 3/1989 | Boss et al. |
|---|---|---|---|
| 4,816,567 | A | 3/1989 | Cabilly et al. |
| 6,566,101 | B1 * | 5/2003 | Shuber et al. ............... 435/91.2 |
| 2005/0159379 | A1 * | 7/2005 | McSwiggen et al. ......... 514/44 |

FOREIGN PATENT DOCUMENTS

| EP | 0368684 | 11/1989 |
|---|---|---|
| EP | 1298220 | 10/2003 |
| EP | 1506777 | 2/2005 |
| WO | WO 88/01649 | 3/1988 |
| WO | WO 93/06213 | 4/1993 |
| WO | WO 98/24884 | 6/1998 |
| WO | WO 01/68828 | 9/2001 |

OTHER PUBLICATIONS

Mummidi et al Evolution of human and non human primate CC chemokine receptor 5 gene and mRNA. Journal of Biological Chemistry 2000 vol. 275, No. 25, pp. 18946-18961.*
Takeda, Jun et al. Sequence of an intestinal cDNA encoding human gastric inhibitory polypeptide precursor. 1987 PNAS vol. 84 pp. 7005-7008.*
Irwin, David et al. Evolution of the vertebrate glucose dependent insulinotropicpolypeptide (GIP) gene. 2006. Comparative Biochemistry and Physiology. Part D1 pp. 385-395.*
Lemmens, Robin et al. Variant on 9p21 strongly assoicates with coronary heart disease but lacks association with common stroke. 2009. European Journal of Human Genetics. vol. 17 pp. 1287-1293.*
Czupryniak et al., Circadian blood pressure variation in morbidly obese hypertensive patients undergoing gastric bypass surgery, Am. J. of Hypertension vol. 18, No. 4, Apr. 2005, pp. 446-451.
Diamond et al.. Monoclonal Antibodies, New England Journal of Medicine, vol. 304. No. 22, May 28, 1981, pp. 1344-1349.
Fehmann et al., Characterization of GIP(1-30) and GIP(1-42) as Stimulators of Proinsulin Gene Transcription, Peptides, vol. 16, No. 6, pp. 1149-1152, Pub 1995.
Gelling et al., GIP6-30amide contains the high affinity binding region of GIP and is a 6¿ 30amide potent inhibitor of GIP1-42 action in vitro. Regulatory Peptides vol. 69, 1997, pp. 151-154.
Gremlich et al., Cloning, Functional Expression, and Chromosomal Localization of the Human Pancreatic Islet Glucose-Dependent Insulinotropic Polypeptide Receptor, Diabetes, vol. 44, 1995, pp. 1202-1208.
Hansotia et al., GIP and GLP-1 as incretin hormones: Lessons from single and double incretin receptor knockout mic, Regulatory Peptides, vol. 128; 2005, pp. 125-134.
Kieffer T.J., GIP or not GIP? That is the question., Trends in Pharmacological Sciences, Elsevier, Amsterdam, NL, vol. 24, No. 3, Mar. 2003, pp. 110-112.
Meier et al., Gastric Inhibitory Polypeptide: the neglected incretin revisited, Regulatory Peptides, vol. 107. 2002. p. 1-13.
Morgan et al., Modifications of Gastric Inhibitory Polypeptide GIP Secretion in Many by a High-Fat Diet, British Journal of Nutrition, vol. 59, No. 3, pp. 373-380, Pub 1988.
Muraoka et al., Polymorphism in exon 4a of the human GLUT4/muscle-fat facilitative glucose transporter gene detected by SSCP, Nucl. Acids Res., vol. 19, No. 15, p. 4313, pub 1991.
Takeda et al., Sequence of an Intestinal Complementary DNA Encoding Human Gastric Inhibitory Polypeptide Precursor, PNAS, 1987, vol. 84, No. 20, pp. 7005-7008.
Winter, Man-made antibodies, Nature, vol. 349, 1991, pp. 293-299.
Yip et al., GIP Biology and Fat Metabolism, Life Sciences, vol. 66, No. 2, 2000, pp. 91-103.

* cited by examiner

*Primary Examiner* — Amanda Shaw

(57) ABSTRACT

The use of the single nucleotide polymorphism (SNP) at position −(97) of the GIP gene for the identification of a cardiovascular disease or of an increased risk for developing a cardiovascular disease in a biological sample taken from an individual to be examined.

9 Claims, 8 Drawing Sheets

FIG 1:

```
  1 aggctcagaaggtccagaaatcaggggaaggagacccctatctgtccttcttctggaaga
 61 gctggaaaggaagtctgctcaggaaataaccttggaagatggtggccacgaagacctttg
121 ctctgctgctgctgtccctgttcctggcagtgggactaggagagaagaaagagggtcact
181 tcagcgctctcccctccctgcctgttggatctcatgctaaggtgagcagccctcaacctc
241 gaggccccaggtacgcggaagggactttcatcagtgactacagtattgccatggacaaga
301 ttcaccaacaagactttgtgaactggctgctggcccaaaaggggaagaagaatgactgga
361 aacacaacatcacccagagggaggctcgggcgctggagctggccagtcaagctaatagga
421 aggaggaggaggcagtggagccacagagctccccagccaagaaccccagcgatgaagatt
481 tgctgcgggacttgctgattcaagagctgttggcctgcttgctggatcagacaaacctct
541 gcaggctcaggtctcggtgactctgaccacacccagctcaggactcgattctgcccttca
601 cttagcacctgcctcagccccactccagaatagccaagagaacccaaaccaataaagttt
661 atgctaagtcgagcccattgtgaaaatttattaaaatgactactgagcact
```

(SEQ ID No.1)

FIG. 2

```
  1 aagctcagaaggtccagaaatcaggggaaggagacccctatctgtccttcttctggaaga
 61 gctggaaaggaagtctgctcaggaaataaccttggaagatggtggccacgaagacctttg
121 ctctgctgctgctgtccctgttcctggcagtgggactaggagagaagaaagagggtcact
181 tcagcgctctcccctccctgcctgttggatctcatgctaaggtgagcagccctcaacctc
241 gaggccccaggtacgcggaagggactttcatcagtgactacagtattgccatggacaaga
301 ttcaccaacaagactttgtgaactggctgctggcccaaaaggggaagaagaatgactgga
361 aacacaacatcacccagagggaggctcgggcgctggagctggccagtcaagctaatagga
421 aggaggaggaggcagtggagccacagagctccccagccaagaaccccagcgatgaagatt
481 tgctgcgggacttgctgattcaagagctgttggcctgcttgctggatcagacaaacctct
541 gcaggctcaggtctcggtgactctgaccacacccagctcaggactcgattctgcccttca
601 cttagcacctgcctcagccccactccagaatagccaagagaacccaaaccaataaagttt
661 atgctaagtcgagcccattgtgaaaatttattaaaatgactactgagcact
```

(SEQ ID No.2)

FIG. 3

```
  1 aggctcagaa ggtccagaaa tcaggggaag gagacccta tctgtccttc ttctggaaga
 61 gctggaaagg aagtctgctc aggaaataac cttggaagat ggtggccacg aagacctttg
121 ctctgctgct gctgtccctg ttcctggcag tgggactagg agagaagaaa gagggtcact
181 tcagcgctct cccctccctg cctgttggat ctcatgctaa ggtgagcagc cctcaacctc
241 gaggccccag gtacgcggaa gggactttca tcagtgacta cagtattgcc atggacaaga
301 ttcaccaaca agactttgtg aactggctgc tggcccaaaa ggggaagaag aatgactgga
361 aacacaacat cacccagagg gaggctcggg cgctggagct ggccagtcaa gctaatagga
421 aggaggagga ggcagtggag ccacagagct ccccagccaa gaacccagc gatgaagatt
481 tgctgcggga cttgctgatt caagagctgt tggcctgctt gctggatcag acaaacctct
541 gcaggctcag gtctcggtga ctctgaccac acccagctca ggactcgatt ctgcccttca
601 cttagcacct gcctcagccc cactccagaa tagccaagag aacccaaacc aataaagttt
661 atgctaagtc gagcccattg tgaaaattta ttaaaatgac tactgagcac t
```

(SEQ ID No.3)

FIG. 4:

MVATKTFALLLLSLFLAVGLGEKKEGHFSALPSLPVGSHAKVSSPQPRGPRY
AEGTFISDYSIAMDKIHQQDFVNWLLAQKGKKNDWKHNITQREARALELASQ
ANRKEEEAVEPQSSPAKNPSDEDLLRDLLIQELLACLLDQTNLCRLRSR (SEQ ID No.4)

FIG. 5

Primer 1: 5'-GCTAATCAGCAGGTCTATGCCTAAT-3' (SEQ ID No.5)

Primer 2: 5'-GGTCTCCTTCCCCTGATTTCTG-3' (SEQ ID No.6)

FIG. 6

Table 1: Characteristics of the study group

|  |  | n | % |
|---|---|---|---|
| Total |  | 1140 |  |
| Gender | female | 362 | 31.8 |
|  | male | 778 | 68.2 |
| Age* |  | 63.8 +/- 10.4 |  |
| BMI*(body mass index) |  | 27.9 +/- 4.3 |  |
| Hypertension |  | 670 | 58.8 |
| Smoker |  | 731 | 64.1 |
| Diabetic (ADA) |  | 364 | 31.9 |
| Myocardial infarction |  | 447 | 39.2 |
| Stroke |  | 86 | 7.5 |

FIG. 7

Table 2: Distribution of GIP genotypes in the study group, based on position 2 in the reference sequence NM_004123.

|  | GIP-G2G | GIP-G2A | GIP-A2A |
|---|---|---|---|
| Patients (n) | 1084 | 55 | 1 |

FIG. 8

Table 3: Associations of the GIP variants G/A at position 2 of the reference sequence NM_004123 with clinical endpoints in the patient group analyzed

|  |  | GIP Genotype | | p value | RR |
|---|---|---|---|---|---|
|  |  | GIP-A2A & A2G (%) | GIP-G2G (%) | | |
| Myocardial infarction | YES | 9 (16.07) | 438 (40.41) | 0.0008 | 3.7 |
|  | NO | 47 (83.93) | 646 (59.59) | | |
| Acute coronary syndrome | YES | 9 (16.07) | 696 (64.21) | 0.0020 | 3.4 |
|  | NO | 47 (83.93) | 388 (35.79) | | |
| Unstable Angina | YES | 9 (16.07) | 356 (32.84) | 0.0066 | 2.9 |
|  | NO | 47 (83.93) | 728 (67.16) | | |
| Premature myocardial infarction | YES | 4 (7.14) | 199 (18.36) | 0.0469 | 2.9 |
|  | NO | 52 (92.86) | 885 (81.64) | | |
| Coronary heart disease (>50% stenosis) | YES | 26 (47.27) | 703 (66.20) | 0.0038 | 2.5 |
|  | NO | 29 (52.73) | 359 (33.80) | | |

SEQUENCE LISTING

<160> NUMBER OF SEQ ID NOS: 6

<210> SEQ ID NO 1
<211> LENGTH: 711
<212> TYPE: DNA
<213> ORGANISM: Homo sapiens

<400> SEQUENCE: 1

```
aggctcagaa ggtccagaaa tcaggggaag gagacccta tctgtccttc ttctggaaga      60
gctggaaagg aagtctgctc aggaaataac cttggaagat ggtggccacg aagacctttg    120
ctctgctgct gctgtccctg ttcctggcag tgggactagg agagaagaaa gagggtcact    180
tcagcgctct ccctccctg cctgttggat ctcatgctaa ggtgagcagc cctcaacctc    240
gaggccccag gtacgcggaa gggactttca tcagtgacta cagtattgcc atggacaaga    300
ttcaccaaca agactttgtg aactggctgc tgcccaaaa ggggaagaag aatgactgga    360
aacacaacat cacccagagg gaggctcggg cgctggagct ggccagtcaa gctaatagga    420
aggaggagga ggcagtggag ccacagagct ccccagccaa gaaccccagc gatgaagatt    480
tgctgcggga cttgctgatt caagagctgt tggcctgctt gctggatcag acaaacctct    540
gcaggctcag gtctcggtga ctctgaccac acccagctca ggactcgatt ctgcccttca    600
cttagcacct gcctcagccc cactccagaa tagccaagag aacccaaacc aataaagttt    660
atgctaagtc gagcccattg tgaaaattta ttaaatgac tactgagcac t              711
```

<210> SEQ ID NO 2
<211> LENGTH: 711
<212> TYPE: DNA
<213> ORGANISM: Homo sapiens

<400> SEQUENCE: 2

```
aagctcagaa ggtccagaaa tcaggggaag gagacccta tctgtccttc ttctggaaga      60
gctggaaagg aagtctgctc aggaaataac cttggaagat ggtggccacg aagacctttg    120
ctctgctgct gctgtccctg ttcctggcag tgggactagg agagaagaaa gagggtcact    180
tcagcgctct ccctccctg cctgttggat ctcatgctaa ggtgagcagc cctcaacctc    240
gaggccccag gtacgcggaa gggactttca tcagtgacta cagtattgcc atggacaaga    300
ttcaccaaca agactttgtg aactggctgc tgcccaaaa ggggaagaag aatgactgga    360
aacacaacat cacccagagg gaggctcggg cgctggagct ggccagtcaa gctaatagga    420
aggaggagga ggcagtggag ccacagagct ccccagccaa gaaccccagc gatgaagatt    480
tgctgcggga cttgctgatt caagagctgt tggcctgctt gctggatcag acaaacctct    540
gcaggctcag gtctcggtga ctctgaccac acccagctca ggactcgatt ctgcccttca    600
cttagcacct gcctcagccc cactccagaa tagccaagag aacccaaacc aataaagttt    660
atgctaagtc gagcccattg tgaaaattta ttaaatgac tactgagcac t              711
```

<210> SEQ ID NO 3
<211> LENGTH: 711
<212> TYPE: DNA
<213> ORGANISM: Homo sapiens

<400> SEQUENCE: 3

```
aggctcagaa ggtccagaaa tcaggggaag gagacccta tctgtccttc ttctggaaga      60
gctggaaagg aagtctgctc aggaaataac cttggaagat ggtggccacg aagacctttg    120
ctctgctgct gctgtccctg ttcctggcag tgggactagg agagaagaaa gagggtcact    180
tcagcgctct ccctccctg cctgttggat ctcatgctaa ggtgagcagc cctcaacctc    240
gaggccccag gtacgcggaa gggactttca tcagtgacta cagtattgcc atggacaaga    300
ttcaccaaca agactttgtg aactggctgc tgcccaaaa ggggaagaag aatgactgga    360
aacacaacat cacccagagg gaggctcggg cgctggagct ggccagtcaa gctaatagga    420
aggaggagga ggcagtggag ccacagagct ccccagccaa gaaccccagc gatgaagatt    480
```

```
tgctgcggga cttgctgatt caagagctgt tggcctgctt gctggatcag acaaacctct    540
gcaggctcag gtctcggtga ctctgaccac acccagctca ggactcgatt ctgcccttca    600
cttagcacct gcctcagccc cactccagaa tagccaagag aacccaaacc aataaagttt    660
atgctaagtc gagcccattg tgaaaattta ttaaaatgac tactgagcac t             711
```

<210> SEQ ID NO 4
<211> LENGTH: 153
<212> TYPE: PRT
<213> ORGANISM: Homo sapiens

<400> SEQUENCE: 4

```
Met Val Ala Thr Lys Thr Phe Ala Leu Leu Leu Ser Leu Phe Leu
1               5                   10                  15

Ala Val Gly Leu Gly Glu Lys Lys Glu Gly His Phe Ser Ala Leu Pro
                20                  25                  30

Ser Leu Pro Val Gly Ser His Ala Lys Val Ser Ser Pro Gln Pro Arg
            35                  40                  45

Gly Pro Arg Tyr Ala Glu Gly Thr Phe Ile Ser Asp Tyr Ser Ile Ala
        50                  55                  60

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
                85                  90                  95

Arg Ala Leu Glu Leu Ala Ser Gln Ala Asn Arg Lys Glu Glu Glu Ala
            100                 105                 110

Val Glu Pro Gln Ser Ser Pro Ala Lys Asn Pro Ser Asp Glu Asp Leu
        115                 120                 125

Leu Arg Asp Leu Leu Ile Gln Glu Leu Leu Ala Cys Leu Leu Asp Gln
    130                 135                 140

Thr Asn Leu Cys Arg Leu Arg Ser Arg
145                 150
```

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5

```
gctaatcagc aggtctatgc ctaat                                           25
```

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6

```
ggtctccttc ccctgatttc tg                                              22
```

USE OF A GIP PROMOTER POLYMORPHISM

The invention relates to the use of single nucleotide polymorphisms (SNPs) for identifying an increased risk of cardiovascular diseases and to primers, probes and polynucleotides suitable for said use. In addition, the invention relates to the use of glucose-induced protein (GIP) for finding active substances for preventing and treating cardiovascular diseases.

In the western world, the group of cardiovascular diseases are the leading cause of death among both sexes, and coronary heart disease, in particular coronary artery disease, can be regarded as the major cause of cardiovascular diseases. Angina, also called angina pectoris, is temporary chest pain or a sensation of pressure that occurs when the heart muscle is not supplied with enough oxygen. When the coronary arteries are narrowed or blocked so that blood flow to the heart muscle cannot increase to meet the increased demand for oxygen, ischemia may occur as a result thereof, causing said pain (i.e. said angina pectoris).

Normally, angina pectoris results from coronary artery disease but may also be caused by other coronary heart diseases. Not every ischemia of the heart muscle causes the pain or sensations of pressure connected with angina pectoris. Ischemia of the heart muscle of this kind, i.e. without angina pectoris, is referred to as silent ischemia. The danger of silent ischemia lies in the fact that the damage to the heart muscle is not noticed by the individual affected. Therefore, the sufferer or the physician in charge are often unable to recognize possible damage to the heart tissue, until said damage ultimately results in a myocardial infarction. For this reason, there is a great demand for diagnostic methods and means for recognizing vascular and, in particular, coronary degenerations (referred to as cardiovascular diseases hereinbelow), which enable a diagnosis, and thus a therapeutic intervention, as early as possible.

It is thus the object of the present invention to provide improved methods for the diagnosis and treatment of cardiovascular diseases.

According to the invention, this object is achieved by using the single nucleotide polymorphism (SNP) at position −97 of the GIP gene for identifying an increased risk of cardiovascular diseases in a biological sample taken from an individual to be examined.

The type of the nucleotide at position −97 is determined here on the basis of common methods. By knowing the type of the nucleotide at said position, the skilled worker can readily determine the risk group to which the individual belongs from whom the sample was derived. Most suitable for this are the 2 most common SNPs at position −97, adenosine (A) and guanosine (G).

The polypeptide hormone gastric inhibitory peptide or glucose-dependent insulinotropic peptide (GIP) is an incretin, which is released from endocrine cells in the duodenum and jejunum due to carbohydrates, fat and amino acids contacting the small intestinal mucosa. The GIP gene is located on chromosome 17q21.3-q22 and codes for a 153 amino acid (aa) protein, prepro-GIP, which gives the 42 aa GIP after the removal of 51 aa and 60 aa from the N terminus and C terminus, respectively. Said GIP is converted, via removal of two further aa from the N terminus by dipeptidyl peptidase IV, into GIP [3-42 amide] (Proc. Natl. Acad. Sci. USA 84:7005-7008, 1987).

The sequence of the GIP gene is known. The coding polynucleotide sequence of said gene can be retrieved under the number NM_004123 at the NCBI Nucleotide Database. The derived protein sequence is also accessible under the number NM_004123 at the NCBI Nucleotide Database. The genomic GIP sequence can likewise be retrieved there under the number NM_004123. NCBI is the National Center for Biotechnology Information (postal address: National Center for Biotechnology Information, National Library of Medicine, Building 38A, Bethesda, Md. 20894, USA; web address: www.ncbi.nhm.nih.gov. Cloning of the GIP gene has been described in Takeda et al., 1987.

The hormone GIP acts as an insulinotropic agent which stimulates insulin release as a function of the existing blood glucose concentration and thus is involved as regulator in maintaining glucose homeostasis. Important GIP functions are the inhibition of gastric acid secretion as well as the inhibition of upper digestive tract motility. The data ascertained in the prior art to determine GIP function are from animal experimental studies (Meier et al., 2002).

The present group of inventions related to one another is based on studies of the GIP gene at the chromosomal level in a clinical cohort of patients, carried out by the inventors to estimate the influence of variations in the GIP gene and/or protein on the clinical and phenotypical picture of a carrier of such variants.

Single nucleotide polymorphisms (SNPs) are variants of a particular nucleotide sequence containing substitutions at individual positions and are well known to the skilled worker.

The prior art describes a length polymorphism in the GIP gene (Nucl Acid Res 19:4313, 1991) and additionally, in publicly accessible data bases, intron polymorphisms as well as an amino acid substitution variant, Ser→Gly, at position 103 of prepro-GIP, see NCBI Database Clusterreport: rs 2291725, Contig NT_010783, mRNA004123, NP004114 found online at www.ncbi.nlm.nih.gov/SNP/snp_ref.cgi?locusld=2695&mrna=NM_004123&ctg=NT_010783&prot=NP_004114&orien=reverse&view+rs+=view+rs+&chooseRs=all).

However, the gene polymorphism in the GIP gene, on which the invention is based, and the implication of GIP, in particular in connection with said gene polymorphism, have been known previously in cardiovascular diseases.

Experiments of the inventors have demonstrated for the first time that variations in the GIP gene occur with statistically significant frequency in humans suffering from cardiovascular diseases. The implication of the GIP gene in this type of disease has never been described before and, in view of the known function of GIP in the area of glucose homeostasis, is to be regarded as completely surprising.

The most frequently occurring nucleotide at position −97, or 2 with respect to the reference sequence of the GIP genetic sequence, is a G. This GIP gene variant is therefore referred to as "wild type" hereinbelow. If, therefore, reference is made in the present application of the substitution or mutation of an nucleobase at the site in question or of a less frequent variant of the GIP gene, then this relates to the presence of a nucleobase other than G at position 2 of the reference sequence (SEQ ID No. 1) or −97, with respect to the translation initiation site.

SEQ ID No. 1 relates to the GIP wild type sequence as defined by NCBI accession number NM_004123; SEQ ID No. 2 relates to the found sequence which has an A at position 2, with respect to the start of the reference sequence, or −97, with respect to the translation initiation site.

The invention furthermore relates to a method for identifying an increased risk of cardiovascular diseases in an individual, which comprises examining a sample taken from an individual, as to whether either or both alleles of the GIP gene have a guanosine in position −97 of the genomic GIP sequence, the presence of said guanosine indicating an increased risk for said individual.

In the study on which the invention is based, the inventors identified seven different gene polymorphisms. Subsequent genotype-phenotype association analyses indicated in this connection that the polymorphism at position 2 of the reference sequence NM_004123 (G→A), in particular, has a statistically significant association to clinical endpoints. Said polymorphism is at position −97, upstream of the ATG translation start codon in the promoter region of the GIP gene (FIG. 1A). Since the polymorphism on which the invention is based is located in a region which is present for transcriptional control and thus expression of the GIP gene and of the corresponding protein, the observed associations are likely to be causally related to the clinical endpoints described hereinbelow, i.e. different expression of the GIP gene, compared to individuals having a nucleotide other than G at position −97, results in altered GIP levels (e.g. cellular or blood levels), having an effect on the occurrence of the clinical endpoints described hereinbelow.

The invention therefore also relates to a method for identifying an increased risk of cardiovascular diseases in an individual, which comprises examining a sample taken from an individual, as to whether, compared to comparative samples from individuals in which a nucleotide other than guanosine is present in position −97 of either or both alleles of the GIP gene, the sample taken contains a changed amount of GIP mRNA and/or protein, the presence of a changed amount indicating an increased risk for said individual.

The change in the amount of GIP, i.e. the change in GIP levels, may be caused here by influencing all levels of expression (transcription, translation, splicing), post-translational modification, transport of the protein or proprotein, or influence on protein stability as well as by influences due to signal transduction pathways acting on GIP expression. It may also be possible for changes of the GIP prepro/pro or mature protein, which act on GIP function, to act similarly to a changed level, or to influence positively or negatively the stability or the transport of prepro/pro or mature GIP and thus have a direct effect on the GIP level. However, since the polymorphism identified herein with the highest significance is located in the untranslated region upstream of the initiation site, influencing the amount of GIP at the level of transcription can be regarded as being most likely causally related to cardiovascular diseases and is preferred in the context of the present invention.

The following abbreviations will be utilized hereinbelow (all positions indicated refer to the position of the nucleotides in the reference sequence NM_004123 in FIG. 1A) and refer to the positions within this sequence, starting from 1, or refer to positions relatively to the site of translation initiation (in this case, the position is preceded by + or −).

GIP-G2G describes the group of persons who have a guanosine (G) at position 2 on both alleles of the GIP gene. Said persons are homozygous with respect to said GIP variant.

GIP-G2A describes the group of persons who have an guanosine (G) at position 2 on one allele of the GIP gene and have an adenosine (A) at position 2 on the other allele of the GIP gene. Said persons are heterozygous with respect to said GIP variant.

GIP-A2A describes the group of persons who have an adenosine (A) at position 2 on both alleles of the GIP gene. Said persons are homozygous with respect to said GIP variant.

Standard abbreviations will be used hereinbelow synonymously for nucleotides and amino acids (i.e. three- or one-letter code).

In the present application, the terms protein sequence, amino acid sequence and polypeptide sequence are used synonymously.

Genetic variations at position 2 of the reference sequence NM_004123 of the GIP gene may be detected, for example,
a) by direct detection of genetic variations at the chromosomal DNA level by way of molecular-biological analysis of the GIP gene which may contain said genetic variations, here in particular the regions around position 2 of the reference sequence NM_004123 of the GIP gene,
b) via detection by measuring GIP mRNA expression,
c) by indirect detection by way of determining the amounts and/or activity of GIP protein present in cells, tissues or body fluids by means of protein-chemical methods.

Genetic variations or polymorphisms at the nucleic acid level (here chromosomal DNA) in the GIP gene at position 2 of the reference sequence NM_004123 may be detected, for example, by
1) methods based on the sequencing of the nucleic acid sequence of said region of the GIP gene (e.g. pyrosequencing, sequencing using radiolabeled or fluorescent dye-labeled nucleotides or via mass spectrometric analysis of said nucleic acid sequence);
2) methods based on hybridization of nucleic acid sequences of said region of the GIP gene (e.g. by means of "DNA microarrays");
3) methods based on the analysis of amplification products of the nucleic acid sequence of said region of the GIP gene (e.g. TaqMan analyses).

Genetic variations or polymorphisms at the nucleic acid level (here chromosomal DNA) in the GIP gene at position 2 of the reference sequence NM_004123 may also be detected, for example, on the basis of measuring expressed GIP mRNA via
1) methods based on the hybridization of nucleic acid sequences of the GIP gene (e.g. by means of "DNA microarrays", Northern blot analyses);
2) methods based on the analysis of amplification products of the nucleic acid sequence of the GIP gene (e.g. "TaqMan" analyses, differential RNA display, representational difference analysis).

In addition, genetic variations or polymorphisms in the GIP gene at position 2 of the reference sequence NM_004123 may be detected via analyzing the amount and/or activity of the GIP protein. The amount and/or activity of the GIP protein may be detected, for example, on the basis of
1) methods based on quantitative detection of the amount of the GIP protein (e.g. Western blot analyses, ELISA test)
2) methods based on functional detection of the activity of the GIP protein via in vitro test systems, for example in human cells, animal cells, bacteria and/or yeast cells.

The detection of the genetic variations or polymorphisms in the GIP gene at position 2 of the reference sequence NM_004123 may be used, for example, as (a) genetic marker for evaluating the risk of myocardial infarction, premature myocardial infarction, acute coronary syndrome, coronary heart disease (>50% stenosis) and unstable angina, (b) marker for preventative treatment of myocardial infarction, premature myocardial infarction, acute coronary syndrome, coronary heart disease (>50% stenosis) and unstable angina in carriers of the corresponding genetic variants, (c) marker for adapting the dosage to be administered of a pharmaceutically active substance for myocardial infarction, premature myocardial infarction, acute coronary syndrome, coronary heart disease (>50% stenosis) and unstable angina, (d) marker for determining the high throughput screening strategy for identifying a pharmaceutically active substance for myocardial infarction, premature myocardial infarction, acute coronary syndrome, coronary heart disease (>50% stenosis) and unstable angina, (e) marker for identifying the relevant individuals or patients for clinical studies in order to test the compatibility, safety and efficacy of a pharmaceutical substance for myocardial infarction, premature myocardial infarction, acute coronary syndrome, coronary heart disease (>50% stenosis) and unstable angina, and (f) basis for developing test systems for analyzing the genetic variation in the GIP gene at the DNA, RNA or protein level.

So far no data connecting clinical effects with GIP variants in humans have been disclosed. Surprisingly, the studies by the inventors have been able to closely connect the presence of the GIP G2A or GIP A2A or G2G, in particular the G2G variant of the GIP gene with a predisposition for coronary heart diseases.

The detection of genetic polymorphisms of the GIP gene, in particular of the GIP G2A or A2A or G2G and, particularly preferably, of the G2G variant may serve, for example, as genetic marker for preventive treatments and preventive measures (medication, lifestyle), (a) in order to delay or even to prevent the onset of a coronary heart disease, preferably coronary artery diseases, particularly preferably angina pectoris, or to alleviate or stop the severity of the later course and the pathological sequelae, or (b) as genetic marker for adjusting a pharmaceutical dosage or (c) as genetic marker for designing a screening for pharmaceuticals or (d) as genetic marker for identifying and, where appropriate, selecting patients in particular treatments or medical studies.

The methods of the invention enable a predisposition for coronary heart diseases to be identified early, thereby making possible the early use of preventive or curative treatment measures, before symptoms such as angina or damage to the heart muscle tissue occur: identification of the polymorphism of the invention by the skilled worker in charge gives a clear indication for the treating or examining physician to screen for an already persisting damage to vessels or heart tissue, or to administer preventive pharmaceuticals, or to suggest a change in lifestyle even before corresponding damage or pain occurs.

In addition, the novel finding of a connection between said variant and the predisposition for coronary heart diseases allows the use of more effective treatments by hinting at a change in the dosage of particular pharmaceuticals or at the necessity of changing the treatment of patients without said mutation in the GIP gene.

Accordingly, the present invention also relates to the use of the single nucleotide polymorphism (SNP) at position −97 of the GIP gene for adjusting the dosage of a pharmaceutical for preventing and/or treating cardiovascular diseases and also to a method for adapting the dosage of a pharmaceutical for treating and/or preventing cardiovascular diseases in individuals, which method comprises examining a sample taken from an individual for the type of the nucleotide at position −97 of the genomic GIP sequence, which is present on either or both alleles of the GIP gene, said dosage being adapted as a function of the type of said nucleotide at position −97.

An advantageous embodiment comprises examining the sample taken from the individual as to whether either or both alleles of the GIP gene have a guanosine at position −97 of the genomic GIP sequence, the dosage of the pharmaceutical being decreased or increased in the presence of a guanosine. Particular preference is given here to both alleles having a guanosine at said position (GIP G2G).

Another advantageous embodiment comprises examining the sample taken from the individual as to whether either or both alleles of the GIP gene have a nucleotide other than guanosine at position −97 of the genomic GIP sequence, the dosage of the pharmaceutical being decreased or increased in the presence of another nucleotide. The other nucleotide is preferably an adenosine.

Moreover, the present invention relates to a method for adapting the dosage of a pharmaceutical for treating and/or preventing cardiovascular diseases in individuals, which method comprises examining a sample taken from an individual, as to whether, compared to comparative samples from individuals in which either or both alleles of the GIP gene have a nucleotide other than G at position −97, the amount of GIP mRNA and/or protein in the sample taken has changed, said dosage being adapted depending on whether the amount of protein and/or mRNA has changed.

The presence of a GIP gene variant, in particular that of the GIP G2A, A2A or GIP G2G variant, has indicator function. The prior art knows a multiplicity of pharmaceuticals for treating or preventing cardiovascular diseases. Since not all pharmaceuticals have the same effect on all patients with the same disease, patients which are treated with cardiovascular pharmaceuticals for the first time normally have to be "adjusted" to the latter, i.e. the treating physician de facto has to test on the individual patient as to which dosage of which pharmaceutical has the desired effect with, at the same time, side effects as small as possible. The disadvantage here is the fact that it is not known beforehand, whether the symptoms in the patient are alleviated or stopped by the pharmaceutical administered (at the given dosage). It is also not possible beforehand to assess accurately, whether said patient will suffer from an undesired side effect.

In this context, identifying the patients as patients having a particular GIP gene variant prior to the treatment, may improve the predictability of the success of treatment with a particular pharmaceutical: the connection of particular variants of the GIP gene with the occurrence of cardiovascular diseases suggests that GIP variations of this kind concur with physiological changes in the individual which ultimately have the effect that said individuals have a higher or lower probability of suffering from a cardiovascular diseases than other individuals. The different efficacy of each pharmaceutical in different individuals must be seen against such a background of different physiological provision of the individual patients. Assigning an individual to such a group of patients with a particular physiological background would allow particular pharmaceuticals which have been proven in clinical studies to be particularly active here to be preferably used and pharmaceuticals which are less active or more likely linked to undesired side effects in this group of patients, compared to patients without said variant, not to be used from the outset.

Normally, a classification of this kind of individual patients prior to a treatment is not possible. Only the knowledge of the connection between the polymorphism on which the invention is based with the occurrence of cardiovascular disease makes this possible. Thus, pharmaceuticals which have shown good success in the treatment of patient groups having the same gene variant in clinical studies may preferably be used on patients having a variation in the GIP gene, whereas pharmaceuticals which are less effective in said patient group or which have a higher probability of undesired side effects than in patient groups having a different gene variant would not be used from the outset. This would reduce the risk for the patient who is "adjusted" to a pharmaceutical and increase the probability of a successful treatment.

Accordingly, a further aspect of the present invention also relates to the use of the SNP at position −97 of the GIP gene for identifying individuals responding to a pharmaceutical for treating and/or preventing cardiovascular diseases.

Such an identification may be carried out, for example, by examining a sample taken from an individual as to whether a. either or both alleles of the GIP gene have at position −97 of the genomic GIP sequence a nucleotide other than guanosine (in particular an A), the presence of said nucleotide being an indicator for the individual from whom the sample has been derived responding to the pharmaceutical, or b. either or both alleles of the GIP gene have at position −97 of the genomic GIP sequence a guanosine, the presence of which is an indicator for the individual from whom the sample has been derived responding to the pharmaceutical, c. the amount of GIP mRNA and/or protein in the sample is different from that in one or more comparative samples from one or more reference individuals, the presence of a different amount being an indicator for the individual from whom the sample has been derived responding to the pharmaceutical.

Such an identification may also be carried out, for example, by examining a sample taken from an individual as to whether a. either or both alleles of the GIP gene have at position −97 of the genomic GIP sequence a nucleotide other than guanosine, the presence of said nucleotide being an indicator for the individual from whom the sample has been derived responding poorly to the pharmaceutical, or b. either or both alleles of the GIP gene have at position −97 of the genomic GIP sequence a guanosine, the presence of which is an indicator for the individual from whom the sample has been derived responding to the pharmaceutical, or c. the amount of GIP mRNA and/or protein in the sample is different from that in one or more comparative samples from one or more reference individuals, the presence of a different amount being an indicator for the individual from whom the sample has been derived responding poorly to the pharmaceutical, with other methods and procedures for identification also being conceivable.

The SNP at position 2 or −97 of the reference sequence (SEQ ID No. 1) is preferably a guanosine or an adenosine.

In this connection, the isolated sample refers to biological material taken from the patient. Biological material may include, inter alia: the cells or preparations or parts of a tissue or an organ or body fluids (e.g. lymph, saliva, blood, skin, connective tissue), or cells, preferably cells which are easy to remove, such as, for example, mucosal cells. Biological material of this kind may be obtained by common techniques such as taking a swab, taking a blood sample, tissue puncture or surgical techniques (e.g. biopsies). The samples are preferably histological specimens, cell preparations, cells, for example mucosal cells, cellular tissue, purified DNA, mRNA or protein or a body fluid such as saliva, lymph or blood or extracts or preparations of said samples thereof. The purification of naturally occurring molecules from cells or tissues and the preparation of cell or tissue extracts are well known to the skilled worker (see also examples of the standard literature listed below). DNA/RNA or protein preparations are obtained therefrom by means of common techniques.

Since GIP has been identified in the present application for the first time as being connected to cardiovascular diseases, the present group of inventions related to one another also concerns the use of a GIP protein or polynucleotide or of a functional fragment thereof for finding active substances for treating and/or preventing cardiovascular diseases.

The use according to present invention allows for the identification of novel substances for the prevention and/or treatment of cardiovascular diseases. The use according to present invention comprises the identification of substances with the desired characteristics as well as the further characterisation of substances already identified to be useful for the prevention and/or treatment of cardiovascular (i.e. the use according to present invention is useful for e.g. compound screening as well as compound profiling).

A substance as to be employed for the different aspects of present invention can be any biological or chemical substance or natural product extract, either purified, partially purified, synthesized or manufactured by means of biochemical or molecular biological methods.

A substance considered as being active in preventing or treating a cardiovascular disease in the sense of the different aspects of present invention can be any substance having an influence of one of the functions of GIP or on the GIP or GIPR amount or steady state level in a biological system or on the expression of GIP or GIPR.

To this end, the substance can modulate any of the functions of GIP (e.g. those as defined above). GIP protein activity can be modulated by the substance e.g by direct interaction and interference of GIP polypeptide/protein or fragments thereof. The substance can also modulate the expression of GIP or GIPR, e.g. on the level of transcription (initiation, elongation, processing, etc), transcript stability, translation. Moreover it can modulate the posttranslational processing, modification, protein folding etc. of GIP. The substance can exert the above effects directly or indirectly (indirectly meaning i.e. by interfering (positively or negatively) with natural signalling cascades having influence on GIP or GIPR function/protein activity/expression etc.). Moreover the substance can also mimic GIP activity (i.e. take over its function/role).

A fragment of GIP can be any polypeptide or polynucleotide that is shorter than the corresponding wild type, e.g. shorter than *homo sapiens* (hs) GIP according to the polynucleotides of SEQ ID No. 1 or 2 or the polypeptide according to SEQ ID No. 1 or SEQ ID No. 4.

A derivative of GIP or of a GIP fragment can be any modification of a GIP polynucleotide, polypeptide or of a fragment thereof. Derivatives comprise, e.g. modifications of the amino acid or nucleotide sequence or any other kind of modification, such as a chemical or biological modification e.g. leading to the stabilization of the polypeptide or polynucleotide (such as phosphorothioate modifications or other kinds of modifications of the nucleic acid backbone or of exchanges of the bonds between amino acids, etc.), or enabling a specific targeting of the polypeptide or polynucleotide to certain cells or facilitating its entry into or uptake by cells (such as cell-permeant phosphopeptides, ortho coupling to cell-permeant peptide vectors, e.g. based on the antennapedia/penetratin, TAT, and signal-peptide based sequences; or coupling to parts of ligands for specific transporters or importers).

A functional fragment of GIP is any fragment (either polypeptide or polynucleotide), which exhibits at least one of the functions of GIP.

The term "functional derivative" of GIP comprises any kind of modification of GIP with respect to the naturally occurring form (either polypeptide or polynucleotide), which at least has one of the functions of GIP. Present invention also comprises functional derivatives of fragments of GIP.

Functions of GIP comprise the functions described above, for example the ability of a GIP protein or protein fragment to increase insulin production or lipoprotein lipase activity, to promote proliferation of the pancreatic β cells, to activate the GIP receptor (GIPR) or to interact in a GIP-typical manner with another molecule, for example another protein such as GIPR or a fragment thereof; with regard to GIP nucleic acids or fragments, for example the ability to interact with other molecules, such as, for example, specific hybridization primers or probes, the ability to control transcription of a downstream coding sequence, to code for GIP, etc.). Functions of GIP comprise also generally the ability of GIP (protein or nucleic acid) or fragments thereof to interact with other molecules (comprising, but not limited to, proteins (i.e. the GIPR), nucleic acids, synthetic molecules).

Another aspect of present invention concerns a method for identifying substances active in preventing or treating a cardiovascular disease comprising:
a. Contacting a GIP protein or functional fragment or derivative thereof with a test substance; and
b. Determining whether the test substance modulates the activity of the GIP protein or functional fragment or derivative thereof.

Another aspect of present invention concerns a method for identifying substances active in preventing or treating a cardiovascular disease comprising:
a. Contacting a cell, which has a detectable amount or or activity of GIP or a functional fragment thereof, with a test substance;
b. Determining whether the test substance is able to modulate the amount or activity of GIP or the functional fragment thereof present in the cell.

Wherein a substance able to detectably increase the GIP amount or activity is considered a substance active in preventing or treating a cardiovascular disease. The detectable amount of GIP can either refer to a detectable amount GIP DNA (cDNA or genomic DNA), protein (prepro/pro/ripe protein) and/or mRNA. The detectable activity can either refer to transcriptional and/or translational and/or protein activity of GIP DNA/mRNA or protein.

Within the different aspects and embodiments of present invention the term modulation refers to activation or an inhibition.

Yet another aspect of present invention concerns a method for identifying substances active in preventing or treating a cardiovascular disease comprising:
a. Contacting a nucleic acid coding for a GIP protein, derivative or fragment thereof with a test substance in a transcriptionally active system;
b. Determining the amount of mRNA coding for GIP protein, derivative or fragment thereof present in said system in presence of said substance;
c. Determining the amount of mRNA coding for GIP protein, derivative or fragment present in said system in absence of said substance;
d. Determining whether the substance is capable of modulating the amount of GIP mRNA present in said system.

Wherein a substance capable of modulating the amount of GIP mRNA present in said system is considered a substance active in preventing or treating a disease associated with or caused by a malfunction of the carbohydrate or lipid metabolism.

A transcriptionally active system is any biochemical or cellular system, which at least has the ability to perform a transcription reaction of a transcription unit. Such systems are well known in the art and comprise cells (e.g. usual laboratory strains or cell lines as well as primary cultures of eucaryotic or prokaryotic cells) as well as in vitro transcription systems or kits (e.g. on basis of cell extracts) which are also commercially available. In case of present invention this can be a biochemical or cellular system expressing prepro-GIP mRNA or expressing mRNA coding for GIP (1-42) or a fragment of GIP (e.g. GIP (3-42) or GIP (1-30).

The determination of the mRNA amount present in the system can be performed according to techniques well known in the state of the art (etc. direct labelling of the product by means of radioactive or fluorescent labelling or product detection by use of specific primers or probes etc.).

Another aspect of present invention concerns a method for identifying substances active in the prevention or treatment of a cardiovascular disease comprising:
a. Contacting a nucleic acid coding for a GIP protein, derivative or fragment thereof with a substance in a translationally active system;
b. Determining the amount of GIP protein, derivative or fragment present in said system in presence of said substance;
c. Determining the amount of GIP protein, derivative or fragment present in said system in absence of said substance;
d. Determining whether the substance is capable of modulating the amount of GIP protein, derivative or fragment present in said system.

Wherein a substance capable of modulating the amount of GIP protein, derivative or fragment present in said system is considered to be a substance active in the prevention or treatment of a disease associated with or caused by a malfunction of the carbohydrate or lipid metabolism.

A translationally active system is any biochemical or cellular system, which at least has the ability to perform a translation reaction of a transcript. Such systems are well known in the art and comprise cells (e.g. usual laboratory strains or cell lines as well as primary cultures of eucaryotic or prokaryotic cells) as well as in vitro translation systems (which are also commercially available, e.g. as kits). For the in vitro translation of a polynucleotide, the polynucleotide is subcloned in a suitable vector, followed by the expression of the polypeptide in suitable buffers and cell extracts (e.g. reticulocyte lysate). Vectors, necessary reagents and protocols with suitable conditions are known in the art and commercially available.

In the context of present invention, the term "polypeptide" refers to a molecule comprising amino acids bound to each other by peptide bonds and which contain at least 10 amino acids coupled to each other in a linear mode. Shorter molecules of this kind are referred to as peptides. The term "protein" refers to molecules comprising at least one polypeptide chain but can also refer to molecules comprising two or more polypeptide chains associated or bound to each other. Thus, the term "protein" comprises the term "polypeptide".

The detection of the GIP protein present in said system can be performed according to techniques well known in the art (e.g. direct radioactive or fluorescent labelling of the translate or the employment of specific antibodies, tagging of the protein and detection of the tag, etc.).

Another aspect of present invention concerns a method for identifying substances active in preventing or treating a cardiovascular disease comprising:
a. Providing a cell transfected with a nucleic acid vector comprising the GIP promoter or a functional fragment thereof operationally coupled to a reporter gene or a functional fragment thereof;
b. Providing a cell transfected with a control vector which comprises a reporter gene or a functional fragment thereof not being operationally coupled to a functional GIP promoter;

c. Determining the reporter gene activity of the cell according to a) and b) in the absence of a substance;
b. Determining the reporter gene activity in the presence of said substance;

Wherein a substance capable of significantly modulating (i.e. increasing or decreasing) reporter gene activity according to a) without significantly modulating reporter gene activity of b) (i.e. capable of specifically increasing GIP promoter activity) is considered to be a substance active in the prevention or treatment of a disease associated with or caused by a malfunction of the carbohydrate or lipid metabolism.

A significant modulation is any modulation (i.e. increase or decrease) higher than the standard deviation, preferably it is at least two times as high as the standard deviation.

The above aspect of present invention is based on a typical reporter gene assay commonly known in the art. To this end, the promoter of choice is inserted into an expression vector suitable for the type of host cell chosen, upstream of the reporter gene of choice in such a way as to allow for an expression of the reporter gene if the promoter is active. The construct is subsequently introduced into the host cell of choice. Suitable methods for transformation or transfection are well known in the art as well as conditions for cell cultivation and detection of reporter gene expression (see e.g. standard literature listed below). Suitable conditions are well known in the art as well as vectors, reporter genes and necessary reagents, which are also commercially available.

A vector is a circular or linear polynucleotide molecule, e.g. a DNA plasmid, bacteriophage or cosmid, by aid of which polynucleotide fragments (e.g. cut out from other vectors or amplified by PCR and inserted in the cloning vector) can specifically be amplified in suitable cells or organisms. Expression vectors enable the heterologous expression of a gene of interest (e.g. a reporter gene), in the host cell or organism. The type of cell or organism largely depends on the aim and the choice lies within the knowledge of the skilled artisan. Suitable organisms for the amplification of a nucleic acid are e.g. mostly single cell organisms with high proliferation rates, like e.g. bacteria or yeast. Suitable organisms can also be cells isolated and cultivated from multicellular tissues, like e.g. cell lines generated from diverse organisms (e.g. SF9 cells from *Spodoptera Frugiperda*, etc.). Suitable cloning vectors are known in the art and commercially available at diverse biotech suppliers like, e.g. Roche Diagnostics, New England Biolabs, Promega, Stratagene and many more. Suitable cell lines are e.g. commercially available at the American Type Culture Collection (ATCC).

For the heterologous expression of a protein or polypeptide, the cell can be any prokaryotic or eucaryotic cell suitable for transfection with a nucleic acid vector and of expressing the gene of interest, e.g. a reporter gene. Possible examples thereof are primary cells or cultured cells, preferably eukaryotic cell cultures, which have originally been obtained, for example, from multicellular organisms or tissues (such as, for example, HeLA, CHO, COS, SF9 or 3T3) or which themselves are unicellular organisms, such as, for example, yeast cells (e.g. *S. pombe* or *S. cerevisiae*) or prokaryotic cell cultures, or *Pichia* or *E. coli*. Cells and samples from tissues may be obtained by known techniques of the prior art (e.g. taking blood samples, tissue puncture or surgical techniques). Suitable for use for the inventive use of GIP are also isolated cells which naturally produce and, where appropriate, secrete GIP, such as, for example, endocrine K cells, it being possible to determine directly the ability of a cardiovascular pharmaceutical to increase or decrease the amount of GIP produced.

In the context of the present application, the term "transfection" refers to the introduction of a nucleic acid vector into a (pro- or eukaryotic) host cell and thus includes the term "transformation". Said transfection may be stable or transient and can be carried out on the basis of common methods.

The GIP promoter region is the part of the GIP gene, which is capable of controlling transcription of a gene product of interest, if the coding sequence of the gene of interest is cloned into a suitable vector, functionally downstream of the promoter/enhancer, and is transfected into a suitable host cell. According to one embodiment, the GIP promoter comprises or consists of the nucleotides 1 to 98 (positions −97 to +1) according to SEQ ID No. 1 or SEQ ID No. 2. Functional fragments of the GIP promoter are GIP promoter fragments which, under the conditions given, can likewise control the transcription of downstream coding sequences. Preferable fragments comprise functional fragments of the GIP promoter according to nucleotides of the nucleotides 1 to 98 of SEQ ID No. 1 or SEQ ID No. 2

A reporter gene can be any gene that allows for an easy quantification of its gene product. A vast variety of reporter genes for eukaryotic or prokaryotic hosts as well as detection methods and necessary reagents are known in the art and commercially available. These comprise e.g. the genes of beta Lactamase (lacZ), Luciferase, Green or Blue fluorescent protein (GFP or BFP), DsRed, HIS3, URA3, TRP1 or LEU2 or beta Galactosidase. These genes encode proteins which can be easily detected by means of a visible (colour or luminescent) reaction (e.g. lacZ, Luciferase). These comprise gene-products which can be easily detected by means of a visible (colour or luminescent) reaction or gene-products conferring resistance towards antibiotics like Ampicillin or Kanamycin when expressed. Other reporter gene-products enable the expressing cells to grow under certain conditions like e.g. auxotrophic genes.

A functional fragment of a reporter gene is any fragment of a given reporter gene that allows for an easy quantification of its gene product.

Within the context of the above aspect of present invention the control vector can be any suitable vector which comprises a reporter gene or functional fragment thereof, but wherein reporter gene expression is not driven by a (functional) GIP promoter. This can e.g. mean that the reporter gene or functional fragment thereof is not operationally coupled to a functional GIP promoter (i.e. either totally devoid of an GIP promoter, comprises a non functional GIP 4 promoter or promoter fragment or wherein the coupling of promoter and reporter gene is not functional). This can also mean that the reporter gene or functional fragment thereof is operationally coupled to another promoter than the GIP promoter (e.g. SV40 or another standard promoter). The functional vector and the control vector can also be transfected to the same cell, but in which case the reporter genes need to be different.

Another aspect of present invention concerns a high throughput screen based on a method according to one of the above novel methods for the identification of active substances (such methods are also called "assays").

Analytical methods or analytical systems, so-called assays, which are used to measure the activity or concentration of defined target molecules (so-called targets, mostly proteins or nucleic acids) as parameter for the effectiveness of a potential pharmaceutical compound, are well known in the state of the art. Assays comprise for example biochemical analytical methods or systems using isolated or partly isolated components that are put together to a reaction mixture within a defined space and time, in which the effectiveness of the potential pharmaceutical compounds can be tested. Other examples of assays comprise biochemical analytical methods or systems, in which the activity of the target molecule and the effectiveness of a potential to influence this activity, can be determined within a cell.

An assay can be any type of analytical method or system to monitor a biological process (see e.g. the above analytical methods). Suitably, molecular cascades and mechanisms representing parts of physiological metabolic pathways but also of pathological conditions are reproduced in cellular or biochemical (in vitro) systems. The pharmacological activity of a potential pharmaceutical compound can thus be determined according to its capability of interfering with or modulating these cascades or mechanisms.

For the use in drug screening, especially the high throughput screening for novel pharmaceutical compounds, the assay needs to be reproducible and is preferably also scalable and robust. In the scope of present invention, high throughput screen means, that a method according to present invention is performed in a very small scale, e.g. on 96, 386 or 1536 well plates in samples of very small volume in the range of few millilitres down to few nanoliters or even less. Thus, a very large amount of samples can be analysed in a short time. High throughput screening mostly comprises the screening of up to approximately 500,000 different compounds for certain ability by means of one single assay. The assay is preferably suitable for high throughput screening of chemical substances for their ability of modulating the activity of the target molecule under investigation. The type of assay depends e.g. on the type of target molecule used (e.g. polypeptide or polynucleotide) and the "read out", i.e. the parameter, according to which the activity of the target molecule is determined (see below).

Different types of assays are commonly known in the state of the art and commercially available from commercial suppliers.

Suitable assays for different purposes encompass radio isotopic or fluorescent assays, for example fluorescence polarization assays (for measuring the interaction of a labelled member with a non-labelled member (e.g. the interaction of labelled protein receptors with their unlabeled ligands).

More examples include cell based assays, wherein a cell line stably (inducible or not; chromosomal or episomal) or transiently expresses a recombinant protein of interest. These assays comprise e.g. reporter gene assays, wherein the regulation of a certain promoter or a signal transduction pathway of a member of a signal transduction cascade is measured according to the activity of a reporter enzyme, the expression of which is under the control of said certain promoter. For this type of assay, a recombinant cell line is constructed containing the reporter gene under the control of a defined promoter that is to be investigated itself or that is regulated by the signalling cascade under investigation. Suitable reporter enzymes and cell lines depend on the aim of the assay, examples are given above and their choice lies within the skill of the artisan (see also above).

Examples suitable for the present invention in this connection are e.g. cellular reporter gene assays in which a reporter gene is under the control of the GIP promoter region (i.e. the sequences located upstream of the translation initiation site, or parts thereof, which are able to cause transcription of a downstream gene and include preferably the region around position −97). It is possible here to examine whether the active compound is able to modify (i.e. to decrease or increase) the amount of reporter gene in the reaction mixture with promoter with the mutation at position −97 in such a way that said amount corresponds to that in a comparative reaction mixture with wild type promoter/enhancer.

Assays for measuring the intracellular ion level are commonly known to persons with skills in the art. For the determination of ion channel activity (which control e.g. intracellular ion concentrations and can thus be employed for measurement of intracellular ion concentrations) e.g. membrane potential sensitive assays and dyes can be used.

For the measurement of cAMP levels, e.g. ALPHAScreen™, fluorescence polarization or HTRF technology are suitable.

For measurement of GPCR activity, e.g. cAMP measurement, for example by means of the AlphaScreen™ cAMP detection system by Packard Bioscience, Ca2+ mobilisation-assays or reporter gene assays are suitable.

For determination of protein phosphorylation e.g. kinase activity, fluorescence polarization assays are commonly known, and other types of assays and "read out" are well known in the state of the art.

According to one embodiment of the different aspects of present invention, GIP is used in this connection as an isolated molecule. In the context of the present invention, the term "isolated" means, with respect to polypeptides/proteins/polynucleotides/nucleic acids and fragments and derivatives thereof, that said molecules have either been purified from natural sources or been prepared recombinantly and purified (the term "purified" also including the term "partially purified", for example in the form of total protein preparations, partial concentrations (e.g. by size fractionation), etc.).

According to a further embodiment of the different aspects of present invention, a GIP polynucleotide is used which comprises sequences upstream of the translation initiation site. According to one preferable embodiment, the GIP polynucleotide has a guanosine at position −97 with respect to the genomic polynucleotide sequence.

Since the GIP gene variant identified as being most significantly connected with the onset of cardiovascular diseases is GIP G2G, a preferred embodiment of the present invention relates to the use of a GIP polynucleotide which comprises sequence regions upstream of the translation initiation site and which has a guanosine at position −97 with respect to the genomic polynucleotide sequence. Thus, according to another preferable embodiment, said GIP polynucleotide is the variant GIP G2G.

Normally, individual SNPs in the wild type sequence of the gene to be studied are not taken into account in the screening for active compounds by using target genes ("molecular targets"). Since the present application has identified, in particular, GIP variants having a guanosine at position −97 of the genomic sequence (GIP G2A and G2G) as being connected with the occurrence of cardiovascular diseases, the use of variants of this kind (in particular against the background of the particular physiological makeup of the cells, which accompanies this) should produce a higher probability of finding active compounds suitable for treating and/or preventing cardiovascular diseases. Since in fact individuals having a genetic and physiological makeup of this kind also are more likely to suffer from cardiovascular diseases, the majority of the active compounds found herein targets precisely this patient group. On the other hand, the use of the GIP G2A and the GIP A2A variants should result in finding active compounds to which in particular patients having this gene variant respond. The use of the GIP G2A or of the A2A variant therefore corresponds to another embodiment of present invention.

Suitable types of assays and other types of readouts are likewise well known to the skilled worker in charge.

In addition, the SNP in the GIP gene is suitable for use in active compound screening using targets other than GIP itself: thus it is possible to use cells in cellular assays for finding active compounds for the treatment and/or prevention of cardiovascular diseases, which compounds have the ability to influence the function and/or activity and/or amount of a target other than GIP, specifically cells whose genome has a defined variant of the GIP gene with respect to position −97, i.e. GIP G2G, GIP G2A or GIP A2A. In this way it is possible to screen specifically for active compounds, even those which intervene in the function of a gene other than the mutated one, against the genetic background which is preferably connected with the disease to be treated.

A further embodiment of the use of the invention accordingly relates to the use of isolated cells having a GIP G2A, A2A and, in particular, a G2G genotype for finding active compounds.

A further aspect of the present invention relates to the use of a means for detecting GIP to detect a predisposition for cardiovascular diseases by analyzing a biological sample taken from the body of an individual to be examined.

Another aspect of the invention relates to the use of a means for detecting GIP for preparing a test kit to determine a predisposition for cardiovascular diseases by analyzing a biological sample taken from the body of the individual to be examined.

In this connection, the presence of a G, and, in particular, of a G on both alleles at position −97, preferably indicates an increased risk.

A means for detecting GIP may be any means suitable for detecting GIP protein or polynucleotide in a biological sample.

A means for detecting the amount (i.e. the steady state level) of GIP in a biological sample may be any means suitable for detecting and quantifying GIP expression, i.e., for example, any means for detecting GIP mRNA or protein. This may be, for example, a primer set which is able to amplify specifically GIP cDNA (for example for use in quantitative RT PCR). Another type of means is, for example, a nucleic acid probe which is able to hybridize under standard conditions specifically to GIP mRNA or cDNA, for example for use in a Northern blot or in microarrays. Another means of this kind is, for example, a specific antibody or an antibody fragment which is able to bind GIP protein, for example for use in immunohistological, immunohistochemical or immunochemical techniques (e.g. detection of GIP protein immobilized to suitable supports such as, for example, membranes, protein chips, ELISA plates, etc.).

The design and synthesis of suitable primers are known in the prior art; such primers may also be obtained commercially. According to a preferred embodiment, these are the primers according to SEQ ID No. 5 and 6. Polynucleotides are sequenced by means of conventional routine methods, for example by using customary laboratory robots which are sold, for example, by companies such as Life Technologies, Applied Biosystems, BioRad, etc.

The design and preparation of suitable probes are likewise known in the prior art (see, for example, the standard literature listed).

The preparation of suitable antibodies or functional fragments thereof is known in the prior art, for example by immunizing a mammal, for example a rabbit, with GIP protein or a fragment thereof, where appropriate in the presence of a suitable adjuvant (Freund's adjuvant or aluminum hydroxide gel, see, for example, Diamond, B. A. et al. (1981) The New England Journal of Medicine: 1344-1349). The polyclonal antibodies produced in the animal as a result of the immunological reaction may subsequently be isolated and purified by means of known methods, for example by column chromatography. Monoclonal antibodies may be obtained, for example, according to the known method by Winter and Milstein (Winter, G. & Milstein, C. (1991) Nature, 349, 293-299). Suitable methods for preparing and purifying monoclonal antibodies are known in the prior art (see standard literature). Examples of known antibodies for detecting GIP are: Cat. # GIP71-A, Alpha Diagnostic International, Inc. Rabbit anti-human GIP antiserum; Alpha Diagnostic International, Inc., 5415 Lost Lane, San Antonio, Tex. 78238 USA; found online at www.4adi.com/; polyclonal GIP (gastric inhibitory peptide) antibody Cat#RDI-PRO 16026; Research Diagnostics Inc Pleasant Hill Road Flanders N.J. 07836 USA; found online at www.researchd.com/index.htm; GIP polyclonal antibody, Cat. # AB953, CHEMICON International, Inc., 28820 Single Oak Drive—Temecula, Calif. 92590, found online at www.chemicon.com/home.asp; Y 101 antibody to human GIP, Yanaihara Institute Inc., found online at www.yanaihara.co.jp/index.html; H-027-02 GIP (human), antibody for immunohistochemistry, and RAB-027-02 GIP (human), antibody for RIA, G-027-02 GIP (human), antibody, purified IgG antibodies, Phoenix Pharmaceuticals, Inc., 530 Harbor Boulevard, Belmont, Calif. 94002, U.S.A., found online at www.phönixpeptide.com/contact_us.html.

In the context of the present group of related inventions, the term antibody or antibody fragment also refers to recombinantly produced antibodies or antigen binding sites thereof, which may also be modified, where appropriate, such as, for example, chimeric antibodies, humanized antibodies, multifunctional antibodies, bi- or oligospecific antibodies or F(ab) or F(ab)$_2$ fragments (see, for example, EP-B1-0 368 684, U.S. Pat. No. 4,816,567, U.S. Pat. No. 4,816,397, WO 88/01649, WO 93/06213 or WO 98/24884).

Conventional immunochemical or immunoradiological methods for detecting an antibody reaction are well known to the skilled worker. Common methods are based, for example, on binding of a specific primary antibody to the antigen to be identified, binding of a secondary antibody which usually recognizes species-specific epitopes on said primary antibody. Binding of said secondary antibody is utilized here in order to generate a detectable signal (for example a radioactive signal, when radiolabeled secondary antibodies are used, or a fluorescent signal, when fluorescence-coupled secondary antibodies are used, or a calorimetrically determinable signal, for example when enzyme-coupled secondary antibodies are used, etc.), see also the literature listed below regarding standard methods.

The present group of inventions related to one another additionally also relates to a test kit for detecting a predisposition for cardiovascular diseases, which test kit comprises at least one means for detecting GIP in biological samples.

In the context of the present invention, the term "kit of parts" (short form: kit) means any combination of components identified herein which have been combined to give a spatially and functionally connected unit which may additionally comprise further parts.

A diagnostic kit according to the present invention comprises at least one means for detecting GIP in a biological sample. Suitably, it may furthermore include suitable buffers and/or further reagents for detecting GIP and/or for preparing or methoding samples and also, where appropriate, instructions for carrying out the particular detection method.

The means for detection may be, for example, a means for detecting GIP mRNA or protein in the sample; preferably a means on the basis of which the amount of GIP mRNA or protein in a sample can be quantified, (for example suitable primers, probes, anti-GIP antibodies, etc.). Another example relates to a means for determining the type of nucleotide at position −97 of the GIP gene, for example a suitable PCR primer set, a probe or a special DNA antibody.

According to a convenient embodiment, the means for detection is a means for detecting a guanosine or adenosine, preferably a guanosine, at position −97 of the GIP gene.

According to another convenient embodiment, the means for detection is a means for detecting the amount of GIP mRNA and/or protein present in a biological sample.

The invention additionally relates to an isolated GIP nucleic acid or a fragment thereof comprising position −97 of the GIP gene, which is characterized by the presence of a nucleotide other than guanosine at position −97, preferably a GIP nucleic acid having an A at position −97 and particularly preferably a nucleic acid having a sequence as defined in SEQ ID No. 2.

In this connection, the means for detection is preferably a genomic probe or a primer set, in particular with primers as defined in SEQ ID No. 5 and 6, or an mRNA probe or an antibody for detecting GIP.

A further aspect of the present group of inventions related to one another is a probe for detecting nucleotide variants in the GIP gene or the GIP mRNA, comprising or consisting of at least 17, preferably 19 to 100, contiguous nucleotides of the genomic GIP sequence comprising position −97.

The invention furthermore relates to primers for amplifying GIP polynucleotides, the amplified polynucleotides comprising position −97 of the GIP gene.

According to a preferred embodiment of the method of the invention, the presence of the variation in the GIP gene is detected by PCR and, where appropriate, subsequent sequencing or with the aid of a genomic nucleic acid probe.

Suitable protocols and reagents for PCR or hybridization with suitable probes which bind, for example, immobilized genomic DNA on suitable supports (e.g. membranes or chips) are well known in the prior art.

A nucleic acid molecule may "hybridize" with another one, if single-stranded forms of both molecules can attach to one another under suitable reaction conditions (temperature and ion concentration of the surrounding medium) in order to form a new double-stranded nucleic acid molecule.

In order to hybridize, the nucleic acid molecules attaching to one another must have complementary sequences. However, depending on the chosen stringency conditions; base mismatches are also possible, without stopping an attachment.

The term "stringency" describes reaction conditions which influence the specificity of hybridization, when two single-stranded nucleic acid molecules attach to one another, and thus also determine how many mismatches or how strong a mismatch between the two molecules are tolerated during attachment. The stringency and thus also the specificity of a reaction here depends inter alia on the temperature and the buffer conditions: thus it is possible to increase stringency and thus also specificity by increasing the temperature and lowering ionic strength. Adequate stringency conditions for attaching two given nucleic acid molecules also depend on the length, the type of nucleic acid molecules, the degree of complementarity. Said parameters are known in the prior art. The higher the degree of correspondence or degree of homology of the two nucleotide sequences, the higher is the melting point Tm of hybrids of the two hybridized nucleic acid molecules. The relative stability of nucleic acid hybrids as a function of the type of the nucleic acids attached to one another here is as follows: RNA:RNA>DNA:RNA>DNA:DNA. Equations for calculating the melting point for hybridization products longer than 100 nucleotides are known in the prior art. In the case of shorter hybridization products (e.g. oligonucleotides), calculation of the melting point depends on the length, with mismatches being more crucial.

Low stringency conditions (i.e. also lower reaction or hybridization specificity) exist, for example, if the hybridization is carried out at room temperature in 2×SSC solution. In contrast, high stringency conditions prevail, for example, when the hybridization is carried out at 68° C. in 0.1×SSC and 0.1% SDS solution. Conditions of moderate stringency are in between.

In the context of the present invention, the term "hybridization under stringent conditions" means those conditions for carrying out the hybridization reaction and subsequent washing steps, under which nucleotide sequences having at least 50, 55, 60, 65, 70, and preferably 75% or more, complementarity to one another remain typically hybridized. The determination of such conditions is well known to the skilled worker in charge and may also be found in the literature of standard laboratory methods (e.g. "Current Protocols in Molecular Biology", John Wiley & Sons, N.Y. (1989), 6.3.1-6.3.6).

Hybridization under stringent conditions in accordance with the present application preferably means here:
1) hybridization of the labeled probe with the sample to be examined at 65° C. or, in the case of oligonucleotides, 5° C. under the melting point of the double strand of oligonucleotide and sample (said melting point is also referred to as annealing temperature), overnight in 50 mM Tris pH 7.5, 1M NaCl, 1% SDS, 10% dextran sulfate, 0.5 mg/ml denatured herring or salmon sperm DNA.
2) washing at room temperature in 2×SSC for 10 minutes.
3) washing at 65° C. (or, in the case of oligonucleotides, 5° C. below the annealing temperature) in 1×SSC/0.1% SDS for 30 minutes.
4) washing at 65° C. (or, in the case of oligonucleotides, 5° C. below the annealing temperature) in 0.2×SSC/0.1% SDS for 30 minutes.
5) washing at 65° C. (or, in the case of oligonucleotides, 5° C. below the annealing temperature) in 0.1×SSC/0.1% SDS for 30 minutes.

Oligonucleotides are polynucleotide fragments, preferably DNA fragments, of from 15 to 30 nucleotides in length. The annealing temperature is calculated here by means of the formula $$Tm=2\times(\text{number of }A+T)+4\times(\text{number of }G+C)° \text{ C.}$$

To prepare a 2×SSC or 0.1×SSC solution, for example a 20×SSC solution is diluted accordingly. The 20×SSC solution consists of: 3 M NaCl/0.3 M sodium citrate×2H$_2$O.

Prior to carrying out hybridization, the polynucleotides to be studied are transferred, where appropriate after electrophoretic fractionation ("Southern" (DNA) or "Northern" blot (RNA)) or without electrophoretic fractionation ("dot" or "slot" blot), to a suitable membrane, for example a nylon or nitrocellulose membrane. The hybridization is carried out with a probe labeled in a suitable manner. Thus, radiolabeling or labeling with fluorescent dyes is convenient, other types of labeling are likewise conceivable. The probe is a single-stranded polyribo- or polydeoxyribonucleotide which is single-stranded from the outset or is usually double-stranded but is used in the denatured state. Said probe binds by way of base pairing to the likewise single-stranded DNA- or RNA-containing biological sample.

According to a further convenient embodiment of the method of the invention, the presence of the variation in the GIP gene is determined by a. providing a biological sample of the individual to be examined, which comprises genomic DNA;
b. preferably isolating the genomic DNA from the sample as defined in a);
c. amplifying a polynucleotide by carrying out a PCR reaction using primers able to amplify a polynucleotide comprising position −97 of the genomic sequence of the GIP gene;
d. sequencing the polynucleotide as defined in c).

According to another preferred embodiment, the presence of the variation in the GIP gene is determined by
a. providing a biological sample of the individual to be examined, which comprises genomic DNA;
b. isolating the genomic DNA from the sample as defined in a);
c. immobilizing the isolated DNA on a suitable support;
d. hybridizing to the immobilized DNA one or more probes which are capable of binding specifically to polynucleotides having a genomic GIP sequence under standard conditions and which have, in this connection, a specificity for a particular nucleotide at position −97 of the GIP gene.

According to a further preferred embodiment of the method of the invention, the change in the amount of mRNA is analyzed by PCR or by using an mRNA probe (i.e. a nucleic acid probe which can hybridize with GIP mRNA or cDNA under standard conditions). This is preferably carried out by
a. providing a biological sample of the individual to be examined, which comprises mRNA;
b. preferably isolating the mRNA from the sample of a);
c. amplifying a polynucleotide by RT-PCR using primers having the ability to amplify a polynucleotide derived from the GIP mRNA;
d. quantifying the amount of the amplified polynucleotide and comparing it with the amount of polynucleotide amplified in at least one reference sample.

According to another preferred embodiment, this is carried out by
a. providing a biological sample of the individual to be examined, which comprises mRNA;
b. isolating the mRNA from the sample of a);
c. transferring the mRNA to a suitable support (e.g. suitable membrane or chip matrix);
d. detecting and quantifying the GIP mRNA on the support by means of at least one suitable probe;
e. comparison with the amount of GIP mRNA in reference samples.

According to another preferred embodiment, such a method comprises the steps of
a. providing a histological sample of the individual;
b. detecting the amount of GIP mRNA by way of hybridization reaction with a suitable mRNA probe, detecting and quantifying the hybridized probe and
c. comparing the amount of GIP mRNA with that in reference samples.

In a further preferred embodiment of the method of the invention, the change in the amount of protein is determined with the aid of at least one antibody. Preferred detection methods here are ELISA, Western blot, protein chip and spectrometric methods.

According to a preferred embodiment, this is carried out by
a. providing a biological sample of the individual to be examined, which comprises protein;
b. preferably isolating the protein from the sample of a);
c. transferring the protein to a suitable support (suitable membrane, ELISA plate, chip matrix, etc.);
d. detecting the protein by means of at least one specific GIP antibody and quantifying the signal on the basis of common methods;
e. comparison with the signal obtained from at least one reference sample.

According to another preferred embodiment, the amount of GIP protein is detected by
a. providing a histological sample of the individual;
b. detecting the amount of GIP protein by way of a binding reaction with a suitable GIP antibody, detecting and quantifying said amount;
c. comparing the amount of GIP protein with that in reference samples.
d. conveniently it is possible here to employ, for example, immunohistochemical or immunoradiochemical detection methods.

In the context of the present group of inventions related to one another, the genomic GIP polynucleotide sequence is preferably the sequence as defined in NM-004123 (SEQ ID No. 1).

According to another preferred embodiment, the genomic GIP polynucleotide sequence has an A at position −97 or 2, with respect to the reference sequence (see SEQ ID No. 2).

According to a preferred embodiment of the present group of inventions related to one another, the individual is a patient having glucose metabolism disorders, preferably a diabetes patient and, particularly preferably, a patient having type II diabetes. In addition, the individual may also be hypertensive and/or may have already suffered a myocardial infarction. The cardiovascular disease is preferably a coronary heart disease (>50% stenosis), a coronary artery disease, myocardial infarction, premature myocardial infarction, acute coronary syndrome or angina pectoris (in particular unstable angina).

Another aspect of present invention concerns the use of a substance active in modulating the amount and/or activity of GIP in a biological system for the manufacture of a medicament for the treatment of prevention of a cardiovascular disease.

Yet another aspect of present invention concerns a method of treating an individual suffering from a cardiovascular disease comprising administering a substance active in modulating the amount and/or activity of GIP in a biological system.

A further aspect of present invention concerns the use of a substance or a combination of substances known to be active in the treatment or prevention of a cardiovascular disease for the manufacture of a medicament for the treatment or prevention of a cardiovascular disease, characterized in that the cardiovascular disease is diagnosed by means of one or both of the methods as described above, optionally together with one or more other diagnostic methods.

Another aspect of present invention concerns a method of treating an individual suffering from a cardiovascular disease comprising,
a) diagnosing the presence of a cardiovascular disease in the individual by means of one or more of the methods as described above, optionally together with one or more other diagnostic methods of the art; and
b) administering a substance or a mixture of substances known to be active in the treatment of a cardiovascular disease.

Substances known to be active in the treatment of cardiovascular diseases are well known in the art. According to one embodiment, the substance or the mixture of substances is active in modulating the amount and/or activity of GIP in a biological system.

The biological system can be any living being or a part thereof. According to one embodiment the biological system is a human being. According to another embodiment the biological system is an animal, e.g. a mammal and preferably a domestic animal or livestock. According to yet another embodiment the biological system is e.g. a cell or a compartment of the body or the compartment of a cell.

According to another aspect of present invention, the substance is capable of modulating the activity or the amount of one or more GIP receptors present in the biological system.

According to another aspect of present invention, the substance is capable of modulating the expression of prepro-GIP, its transcription, its translation, its protein or mRNA-stability, its posttranslational modification, the processing of prepro-GIP to GIP or the cellular release of GIP.

According to another aspect of present invention, the substance is capable of modulating the activity or amount of one or more proteases involved in the processing of prepro-GIP to GIP present in the biological system such as dipeptidyl peptidase IV.

The substance can e.g. be a GIP receptor antagonist.

Such antagonists are known in the art. These cover, e.g. regulatory peptides, such as GIP(6-30)-NH$_2$ (see Gelling et al., 1997) or GIP(7-30)-NH$_2$ (see Tseng et all, 1999).

According to one embodiment the substance is a low molecular weight molecule. Such molecules are known in the art, such as methylidene hydrazide compounds. Such compounds, their structure and preparation are e.g. disclosed in the EP 1 506 777 A1.

The isolated sample used for the methods, use or test kit of the present invention is preferably a human sample and the individual to be examined is preferably a human being. Said sample may be in particular: a histological sample, a biopsy sample, a cell (e.g. mucosal cells), a cell extract, cellular tissue, body fluid, preferably blood, saliva, lymph or urine.

The invention will be illustrated in more detail below on the basis of examples which are not to be regarded as limitation, in combination with the figures and tables:

DESCRIPTION OF THE FIGURES

FIG. 1: subregion of the genomic sequence of the human GIP gene as defined in NM_004123 (SEQ ID No. 1); position 2, or position −97 with respect to the start of translation, is depicted in bold type; the translation initiation site is underlined.

FIG. 2: subregion of the genomic sequence of the human GIP gene having an adenosine (bold type) at position 2 or position −97, with respect to the start of translation (SEQ ID No. 2); the translation initiation site is underlined.

FIG. 3: coding sequence of the human GIP gene as defined in NM_004123 (SEQ ID No. 3). The coding sequence are positions 99 to 560 of NM_004123 (depicted in bold type).

FIG. 4: derived protein sequence of the human GIP gene as defined in NM_04123 (SEQ ID No. 4)

FIG. 5: primer for amplifying the region around position 2 of the genomic sequence of the human GIP gene (SEQ ID Nos. 5 and 6).

FIG. 6: Table 1 shows the characteristics of the patient group examined (study group).

FIG. 7: Table 2 shows the distribution of GIP genotypes in the study group, based on position 2 in the reference sequence NM_004123 (SEQ ID NO:1).

FIG. 8: Table 3 shows the associations of the GIP variants G/A at position 2 of the reference sequence NM_004123 (SEQ ID NO:1) with clinical end points in the patient group analyzed.

EXAMPLES

Example 1

SNP Detection by Sequencing and Analysis of the Results

Amplification of Genomic Regions in the Promoter of the Gene of Gastric Inhibitory Peptide (GIP)

Oligonucleotides (Primers) for Amplification:

To detect the nucleotide substitution, A for G, at position 2 in the GIP sequence with the reference number NM_004123 (SEQ ID NO: 1), the following primers were used:

```
Primer 1:
5'- GCTAATCAGCAGGTCTATGCCTAAT-3'     (SEQ ID NO: 5)

Primer 2:
5'- GGTCTCCTTCCCCTGATTTCTG-3'        (SEQ ID NO: 6)
```

PCR Protocol for Amplification:

Reagents used are from Applied Biosystems (Foster City, USA):

20 ng of genomic DNA; 1 unit of TaqGold DNA polymerase; 1× Taq polymerase buffer; 500 µM dNTPs; 2.5 mM MgCl$_2$; 200 nM of each amplification primer pair (sequences under 1.A); H$_2$O to 5 µl.

PCR Amplification Program for Genotyping:

| | |
|---|---|
| 95° C. for 10 min | ×1 cycle |
| 95° C. for 30 s | ×2 cycles; |
| 70° C. for 30 s | |
| 95° C. for 30 s | ×2 cycles; |
| 65° C. for 30 s | |
| 95° C. for 30 s | ×2 cycles; |
| 60° C. for 30 s | |
| 95° C. for 30 s | ×40 cycles; |
| 56° C. for 30 s | |
| 72° C. for 30 s | |
| 72° C. for 10 min | ×1 cycle; |
| 4° C. for 30 s | |

Identification of SNPs

Protocol for Minisequencing and Detection of SNPs

All reagents are from Applied Biosystems (Foster City, USA). 2 µl of purified PCR product, 1.5 µl of BigDye terminator kit, 200 nM sequencing primer (for sequences, see under 1.A), H$_2$O to 10 µl.

Amplification Program for Sequencing:

| | |
|---|---|
| 96° C. for 2 min | ×1 cycle; |
| 96° C. for 10 s | ×30 cycles; |
| 55° C. for 10 s | |
| 65° C. for 4 min | |
| 72° C. for 7 min | ×1 cycle; |
| 4° C. for 30 s | |

Analysis of Sequencing Products:

The sequences were firstly analyzed using the "Sequenz Analyse Software" (Applied Biosystems, Foster City, USA) to obtain the raw data and then methoded with Phred, Phrap, Polyphred and Consed. Phred, Phrap, Polyphred and Consed

Example 2

Statistical Analysis of the Identified SNPs

For the present patent application, the G2A polymorphism of the reference sequence NM_004123 GIP was studied for association with clinical parameters in 1140 patients (table 1). The distribution of the GIP genotypes of position 2, based on the reference sequence NM_004123 in the patient group analyzed is depicted in table 2. All statistical analyses were carried out with SAS version 8.2 (SAS Institute GmbH, Heidelberg, Germany).

Associations of the GIP variants G/A at position 2 of the reference sequence NM_004123 with clinical endpoints in the patient group analyzed can be found in table 3. The p value is a parameter relating to the statistical significance of the associations observed, RR (risk ratio) is a parameter relating to the increased risk of the occurrence of the clinical end point indicated in patients having GIP-2G2 in comparison with patients having GIP-A2A and GIP-A2G. RR was calculated with adjustment of the patient groups with respect to age, sex, smoker, blood pressure and cholesterol level.

The patient group analyzed revealed statistically significant associations of the homozygous carriers of the GIP variant G2G with myocardial infarction, acute coronary syndrome, unstable angina, tendency to premature myocardial infarction and coronary heart disease, in comparison with carriers of the GIP variants GIP-G2A and GIPA2A. After carrying out a logistic regression in order to calculate the risk ratio (RR), a 3.7 fold increased risk of myocardial infarction, a 3.4 fold increased risk of acute coronary syndrome, a 2.9 fold increased risk of unstable angina, a 2.9 fold increased risk of premature myocardial infarction and a 2.5 fold increased risk of coronary heart diseases were found for carriers of the GIP-G2G variant, in comparison with carriers of the GIP-G2A and GIP-A2A variants (table 3).

REFERENCES

Standard Literature of Laboratory Methods:

(Unless stated otherwise, the laboratory methods mentioned herein are or can be carried out according to the standard literature listed below.)

Sambrook et al. (1989) Molecular Cloning: A Laboratory Manual. Second edition. Cold Spring Harbor Laboratory Press, Cold Spring Harbor, N.Y. 545 pp;

Current Protocols in Molecular Biology; regularly updated, e.g. Volume 2000; Wiley & Sons, Inc; Editors: Fred M. Ausubel, Roger Brent, Robert Eg. Kingston, David D. Moore, J. G. Seidman, John A. Smith, Kevin Struhl.

Current Protocols in Human Genetics; regularly updated; Wiley & Sons, Inc; Editors: Nicholas C. Dracopoli, Honathan L. Haines, Bruce R. Korf, Cynthia C. Morton, Christine E. Seidman, J. G. Seigman, Douglas R. Smith.

Current Protocols in Protein Science; regularly updated; Wiley & Sons, Inc; Editors: John E. Coligan, Ben M. Dunn, Hidde L. Plogh, David W. Speicher, Paul T. Wingfield.

Molecular Biology of the Cell; third edition; Alberts, B., Bray, D., Lewis, J., Raff, M., Roberts, K., Watson, J. D.; Garland Publishing, Inc. New York & London, 1994;

Short Protocols in Molecular Biology, 5th edition, by Frederick M. Ansubel (Editor), Roger Brent (Editor), Robert E. Kingston (Editor), David D. Moore (Editor), J. G. Seidman (Editor), John A. Smith (Editor), Kevin Struhl (Editor), October 2002, John Wiley & Sons, Inc., New York Transgenic Animal Technology A Laboratory Handbook. C. A. Pinkert, editor; Academic Press Inc., San Diego, Calif., 1994 (ISBN: 0125571658)

Gene targeting: A Practical Approach, $2^{nd}$ Ed., Joyner A L, ed. 2000. IRL Press at Oxford University Press, New York;

Manipulating the Mouse Embryo: A Laboratory Manual. Nagy, A, Gertsenstein, M., Vintersten, K., Behringer, R., 2003, Cold Spring Harbor Press, New York;

Literature concerning GIP or substances modulating GIP:

Gremlich S., Porret A, Hani E H, Chemf D, Vionnet N, Froguel P, Thoret B; Cloning, functional expression, and chromosomal localization of the human pancreatic islet glucose-dependent insulinutropic polypeptide receptor. Diabetes 1995, 44:1202-8

Takeda J, Seino Y, Tanaka K, Fukomoto H, Kayano T, Takahashi H, Mitani T, Kurono. M, Suzuki T, To be T, Imura H; Sequence of an Intestinal cDNA Encoding Human Gastric Inhibitory Polypeptide Precursor; PNAS 1987, vol. 84 No. 20; 7005-7008

Gelling R W, Coy D H, Pederson R A, Wheeler M B, Hinke S, Kwan T, Mcintosh C H S; $GIP_{6-30amide}$ contains the high affinity binding region of GIP and is a potent inhibitor of $GIP_{1-42}$ action in vitro; Regulatory Peptides 69 (1997) 151-154;

Tseng C C, Zhang X Y, Wolfe M; Effect of GIP and GLP-1 antagonists on insulin release in the rat; AJ Physiology-Endocrinology 276: 1049-1054, 1999

Hansotia T and Drucker D J; GIP and GLP-1 as incretin hormones: Lessons from single and double incretin receptor knockout mice; Regulatory Peptides 128 (2005) 125-134;

Fehmann H C, Göke B; Charakterization of GIP(1-30) and GIP (1-42) as stimulators of proinsulin gene transcription; Peptides Vol. 16 No. 6, 1149-1152, 1995

Yip R G C, Wolfe M; GIP biology and fat metabolism; Life Sciences, Vol. 66, No. 2, 91-103, 2000

Meier J J, Nauck M A, Schmidt W E, Gallwitz B; Gastrick Inhibitory Polypeptide: the neglected incretin revisited; Regulatory Peptides 107 (2002) 1-13

What is claimed is:

1. A method for identifying a human individual with a cardiovascular disease or identifying a human individual with an increased risk for developing a cardiovascular disease comprising: a) isolating a sample comprising a genomic GIP sequence from the human individual, b) detecting in said sample a guanosine at position 2 of SEQ ID NO: 1 in both alleles of the genomic GIP sequence, and c) determining that said human individual with two guanosine alleles at position 2 of SEQ ID NO: 1 has a cardiovascular disease or has an increased risk for developing a cardiovascular disease in comparison to a human individual with one or two adenosine alleles at position 2 of SEQ ID NO: 1, wherein said cardiovascular disease is selected from the group consisting of coronary heart disease, unstable angina, acute coronary syndrome, myocardial infarction and premature myocardial infarction.

2. The method according to claim 1, wherein the method is a high throughput assay (HTS).

3. The method according to claim 1, wherein said detecting comprises using a GIP polynucleotide that comprises a sequence located upstream from a GIP translation initiation site.

4. The method as claimed in claim 1, wherein the alleles at position 2 of SEQ ID NO: 1 are identified by PCR or a nucleic acid probe.

5. The method as claimed in claim 4, wherein the alleles at position 2 of SEQ ID NO: 1 are determined by:
   a) carrying out a PCR reaction using primers able to amplify the genomic GIP sequence comprising position 2 of SEQ ID NO: 1, and
   b) sequencing the genomic GIP sequence that was amplified.

6. The method as claimed in claim 4, wherein the alleles at position 2 of SEQ ID NO: 1 are determined by:
   a) immobilizing the genomic GIP sequence on a suitable support; and
   b) hybridizing to the immobilized genomic GIP sequence one or more allele specific probes which are capable of detecting the alleles present at position 2 of SEQ ID NO: 1.

7. The method as claimed in claim 1 wherein the human individual has a glucose metabolism disorder.

8. The method as claimed in claim 1 wherein the human individual suffers from hypertension and/or has already suffered a myocardial infarction.

9. The method as claimed in claim 1 wherein the sample is selected from the group consisting of a histological sample, a biopsy sample, a cell extract, and body fluid.

* * * * *

UNITED STATES PATENT AND TRADEMARK OFFICE
CERTIFICATE OF CORRECTION

Page 1 of 1

PATENT NO. : 8,084,198 B2
APPLICATION NO. : 11/913873
DATED : December 27, 2011
INVENTOR(S) : Kozian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 729 days.

Signed and Sealed this
Seventeenth Day of April, 2012

David J. Kappos
*Director of the United States Patent and Trademark Office*